United States Patent
Van Oort

(10) Patent No.: US 6,216,037 B1
(45) Date of Patent: Apr. 10, 2001

(54) PACEMAKER SYSTEM WITH SIMPLIFIED ATRIAL CAPTURE DETECTION BASED ON QT INTERVAL

(75) Inventor: Geeske Van Oort, Nieuwleusen (NL)

(73) Assignee: Medtronic Inc,, Minneapolis, MN (US)

( * ) Notice: Subject to any disclaimer, the term of this patent is extended or adjusted under 35 U.S.C. 154(b) by 0 days.

(21) Appl. No.: 09/239,018

(22) Filed: Jan. 29, 1999

(51) Int. Cl.[7] ........................................ A61N 1/37
(52) U.S. Cl. ............................................... 607/28
(58) Field of Search ................................. 607/28

(56) References Cited

U.S. PATENT DOCUMENTS

| | | | |
|---|---|---|---|
| 3,920,024 | 11/1975 | Bowers | 128/419 PG |
| 4,686,988 | 8/1987 | Sholder | 128/419 PT |
| 5,476,486 | 12/1995 | Lu et al. | 607/28 |
| 5,476,487 | 12/1995 | Sholder | 607/28 |
| 5,601,615 | 2/1997 | Markowitz et al. | 607/28 |
| 5,674,254 | * 10/1997 | Krieken | 607/28 |
| 5,683,426 | 11/1997 | Greenhut et al. | 607/9 |

\* cited by examiner

*Primary Examiner*—William E. Kamm
(74) *Attorney, Agent, or Firm*—Thomas F. Woods; Michael J. Jaro; Harold Patton

(57) ABSTRACT

There is provided a system and method for determining, in a DDD or DDD(R) pacing system, when a delivered atrial pace pulse has failed to capture the patient's atrium. Each cycle, following a delivered ventricular pace pulse, or every N cycles a measure of change in QT interval is obtained and compared to stored criteria. When an atrial pulse has achieved capture, the difference in QT from the last beat will be small, normally less than 2 ms. However, if there has not been atrial capture, the delivered ventricular pace pulse is in fact asynchronous with respect to the atrium, and under these circumstances the change in QT is greater than 2 ms, e.g., in the range of 2–10 ms. Accordingly, when the pacemaker sees a change in QT within the 2–10 ms range, this indicates failure of capture, and responsive action is taken by either directly incrementing the energy level of the atrial pace pulses, or performing an atrial threshold search and then resetting the atrial pace energy level.

11 Claims, 4 Drawing Sheets

PACEMAKER SYSTEM WITH SIMPLIFIED ATRIAL CAPTURE DETECTION BASED ON QT INTERVAL

FIELD OF THE INVENTION

This invention relates generally to implantable dual chamber pacemaker systems and, more particularly, to a pacemaker system with the capability of for continuously monitoring for loss of capture following delivered atrial pulses.

BACKGROUND OF THE INVENTION

As is well known in the art, cardiac pacemaker systems provide for delivery of timed pacing pulses designed to cause the myocardium of the heart to contract, or beat, so as to compensate for the inability of the heart to provide normal beating. Stimulation pulses, or pacing pulses generally are set at a programmable energy level, involving both pulse width (duration) and amplitude, so as to provide pulses of sufficient energy to actually stimulate the heart into a contraction. When a delivered pace pulse is successful in so stimulating the heart to contraction, it is said to have "captured" the heart, whereas failure to stimulate the heart is described as "loss of capture" (LOC). It is thus an important function of the pacemaker to control the pulse energy so that it is sufficiently above the stimulation threshold to generally ensure capture, but yet avoid excessively high energy pulses and thereby minimize battery depletion.

As is well known, the stimulation threshold for a patient, in both the atrium and the ventricle, can fluctuate both short term and long term. Because stimulus threshold may increase for a variety of reasons, it has become state of the art to periodically conduct a threshold tests, and to readjust the pulse energy in accordance with any newly determined threshold. The pacing literature provides many examples of such threshold tests. An early example of an automatic threshold tracking pacemaker is found in U.S. Pat. No. 3,920,024 (Bowers), where the stimulus energy is initially set at a high enough energy to ensure capture, and then is reduced by successive increments until capture is lost. In this technique, capture must be detected directly by sensing the evoked signal, which remains a difficult task. Further, when the pulse energy is dropped low enough so that capture is lost, a back-up pulse must be delivered so as to avoid skipping a heartbeat.

Due to the inherent difficult of sensing an evoked depolarization at or near the site of delivering a stimulus pulse, a wide variety of different approaches have been taken in an attempt to reliably determine when a delivered pacing pulse has not resulted in capture. See U.S. Pat. No. 5,601,615, Medtronic, Inc., which presents a summary of such approaches that are to be found in the patent literature. These approaches include separate electrodes or electrode systems and amplifiers for sensing evoked responses; physiologic sensors for determining mechanical changes in the heart or changes in the blood when the heart is captured, etc.

This invention addresses primarily the need in a DDD, or DDD(R) pacing system to determine on an ongoing basis whether a delivered atrial pacing pulse has result in capture of the atrium. The standard technique with regard to this problem is to undertake a test, either initiated from an external programmer or initiated automatically by an implanted pacemaker, to obtain information to determine whether an atrial pace pulse achieves capture. See, for example, U.S. Pat. No. 5,476,486, where the amplitude of the atrial pacing pulse is decreased progressively, while the following R wave is monitored; the absence of an R wave indicates loss of atrial capture. However, if the patient has a high degree of AV block, and ventricular pacing is required, this method cannot be used. Note also the aforementioned U.S. Pat. No. 5,601,615, which employs a test procedure for delivering atrial pacing pulses at an early atrial escape interval which precedes the anticipated natural atrial contraction, and looking for a ventricular sense within the latter portion of the AV delay interval. If the ventricular sense is not found within such latter portion, then failure to capture is assumed. Other examples from the prior art require special circuitry and/or leads with specific electrode arrangements designed to detect the occurrence of an evoked response within an anticipated time following delivery of an atrial pace pulse.

What is needed in the art is a pacemaker with the capability of reliably detecting when a delivered atrial pace pulse has evoked a P wave, without requiring special tests or additional components or circuitry which consume energy and add to the bulk and cost of the system. Specifically, there is a substantial need for a pacemaker which utilizes already available information and thus requires no special circuitry or test procedures, for reliably determining on an ongoing basis when a delivered atrial pacing pulse has not captured the atrium. The need is particularly evident in the specific situation where, following lack of capture but before timeout of the AV interval, a spontaneous atrial contraction takes place which the pacemaker does not sense. In such a situation a ventricular pace pulse is delivered asynchronously with respect to the intrinsic atrial contraction. If such asynchronous pacing is permitted to continue, the patient has lost the important benefit of synchronous pacing.

SUMMARY OF THE INVENTION

It is an object of this invention to provide an implantable DDD pacemaker with a simple but reliable method for continually determining whether a delivered atrial pace pulse (AP) has resulted in capture of the atrium, the method utilizing QT interval data alone for determination of capture or LOC.

In accordance with the above object, the pacemaker continuously, on a cycle-by-cycle basis, measures and stores the QT interval, and makes a determination of change in QT interval, i.e., $\Delta QT = {}^*QT - QT_{PREV}{}^*$. The $\Delta QT$ variable is compared to a lower limit such as 2 ms and a higher limit such as 10 ms, and when $\Delta QT$ is within this range there is a determination of LOC. With the determination of LOC, appropriate responsive action is taken, such as adjusting the AP level upward by a predetermined amount, or initiating a threshold search which culminates in a new AP level safely above the atrial stimulus threshold.

DESCRIPTION OF THE PREFERRED EMBODIMENTS

Figure 1:
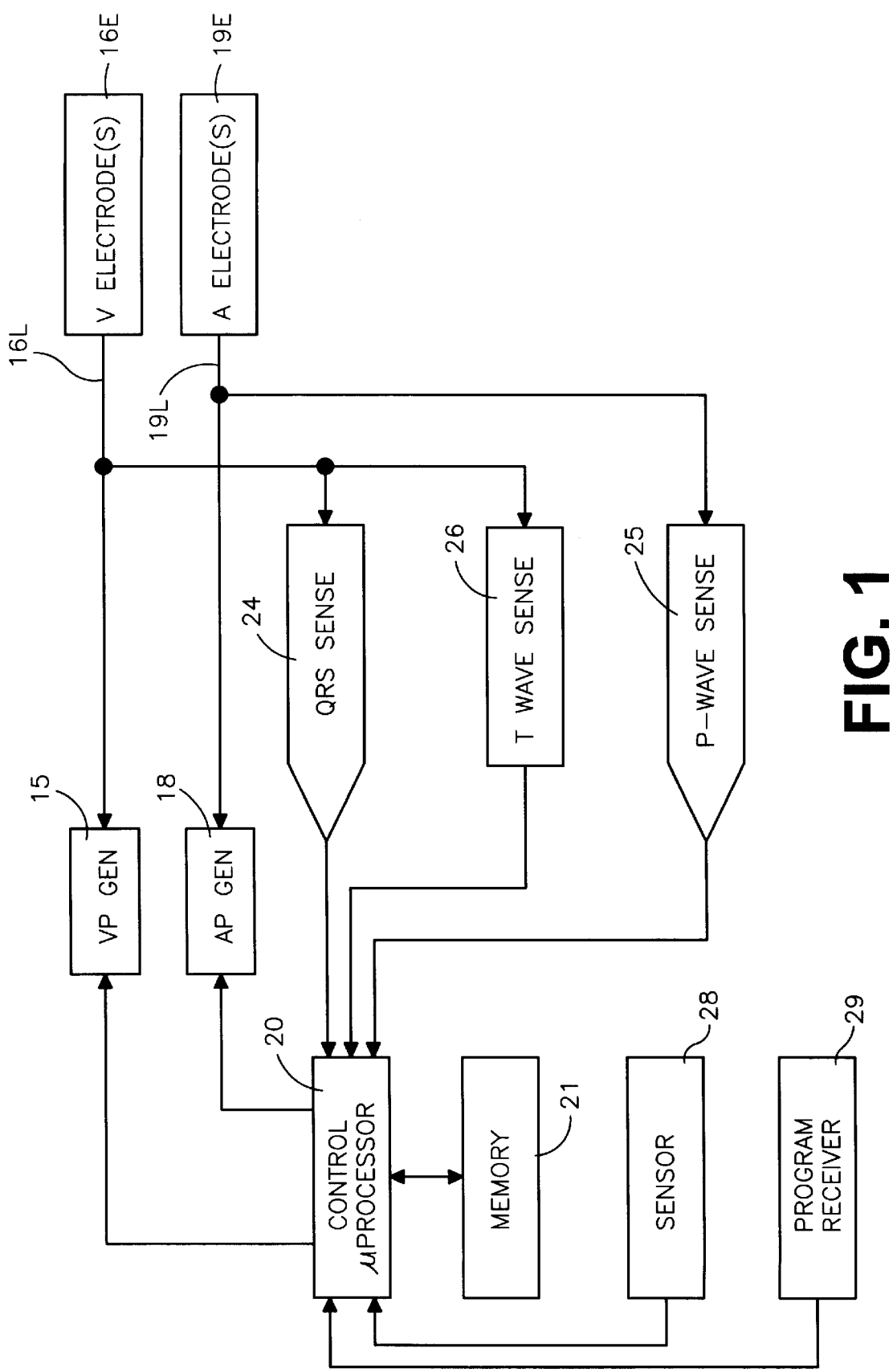
FIG. 1 is a block diagram showing the primary components of a pacing system in accordance with this invention.

Referring now to FIG. 1, there is shown a block diagram illustrating the primary components of a pacemaker system in accordance with this invention. A ventricular pulse generator 15 is controlled under control block 20 to generate ventricular pacing pulses, which are delivered to the patient's heart through lead 16L to ventricular electrodes 16E. Likewise, for a DDD-type dual chamber pacemaker, atrial pulse generator 18 also is controlled by block 20, and generates atrial pace pulses which are delivered through lead 19L to atrial electrodes 19E. The signals sensed at the ventricular electrodes are amplified at QRS circuitry 24 and T wave sense circuitry 26, respectively, the outputs of which are connected to control block 20. Signals sensed in the atrium by atrial electrode or electrodes 19E are amplified at P wave sense circuitry 25, and connected to control block 20. Control block 20, in the preferred embodiment, contains a microprocessor, and is in two-way connection with suitable memory 21. As discussed hereinbelow, the logic steps taken in the practice of this invention are preferably handled by software, including the QT analysis depicted in FIG. 3. Also shown in FIG. 1 is a sensor or sensors 28, which can be used for rate control in a known manner; the QT interval obtained from the signals outputted by sense circuits 24 and 26 can also be used for rate control. A program receiver (and transmitter) 29 is used to receive program instructions from an external programmer, which are downloaded through control block 20. In the context of this invention, the determination of when change of QT signifies LOC can be changed by reprogramming or by downloading a replacement routine.

Figure 2:
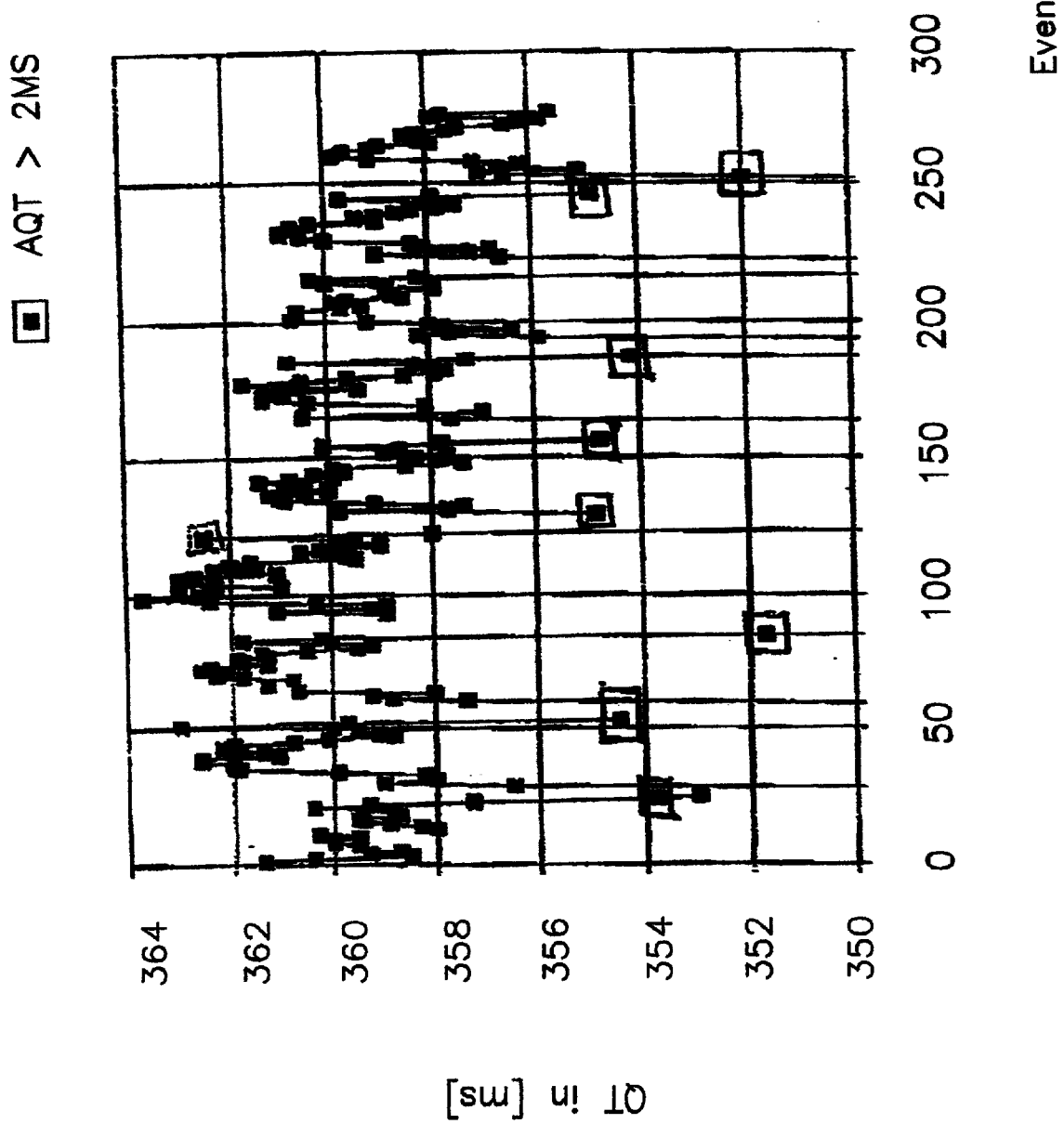
FIG. 2 is a plot showing variations in QT interval at a steady pacing rate of 80 bpm, and illustrating QT variations following atrial LOC.

Referring now to FIG. 2, there is shown a plot of QT interval values for successive cycles, or event, where APs and Vps were delivered at a constant rate of 80 ppm. Generally, changes from cycle to cycle are within 2 ms; but where there has been a failure to capture, the variation in QT interval is greater, and more than 2 ms. In such situations, the slower occurring natural atrial signal comes after the AP is delivered, and the VP is then asynchronous with regard to the actual atrial contraction. It is believed that the asynchronous nature of the ventricular contraction affects the time between depolarization and repolarization, or QT interval. Note that in some cases the QT interval has dropped such that it is off the bottom of the chart, i.e., the chart does not show a QT interval; these are instances where there was a spontaneous atrial signal (NAS) that followed delivery of an AP, followed by a spontaneous QRS and T wave, or NVS; or, the NAS may be undersensed, and followed by a fusion beat. In any event, such events can occasionally occur in patients for whom a DDD or DDD(R) is indicated, and such great QT interval differences should not be interpreted as failure to capture. For this reason, the "failure" range is set at greater than a 2 ms change, but less than an upper limit, e.g., 8 to 10 ms.

Figure 3A:
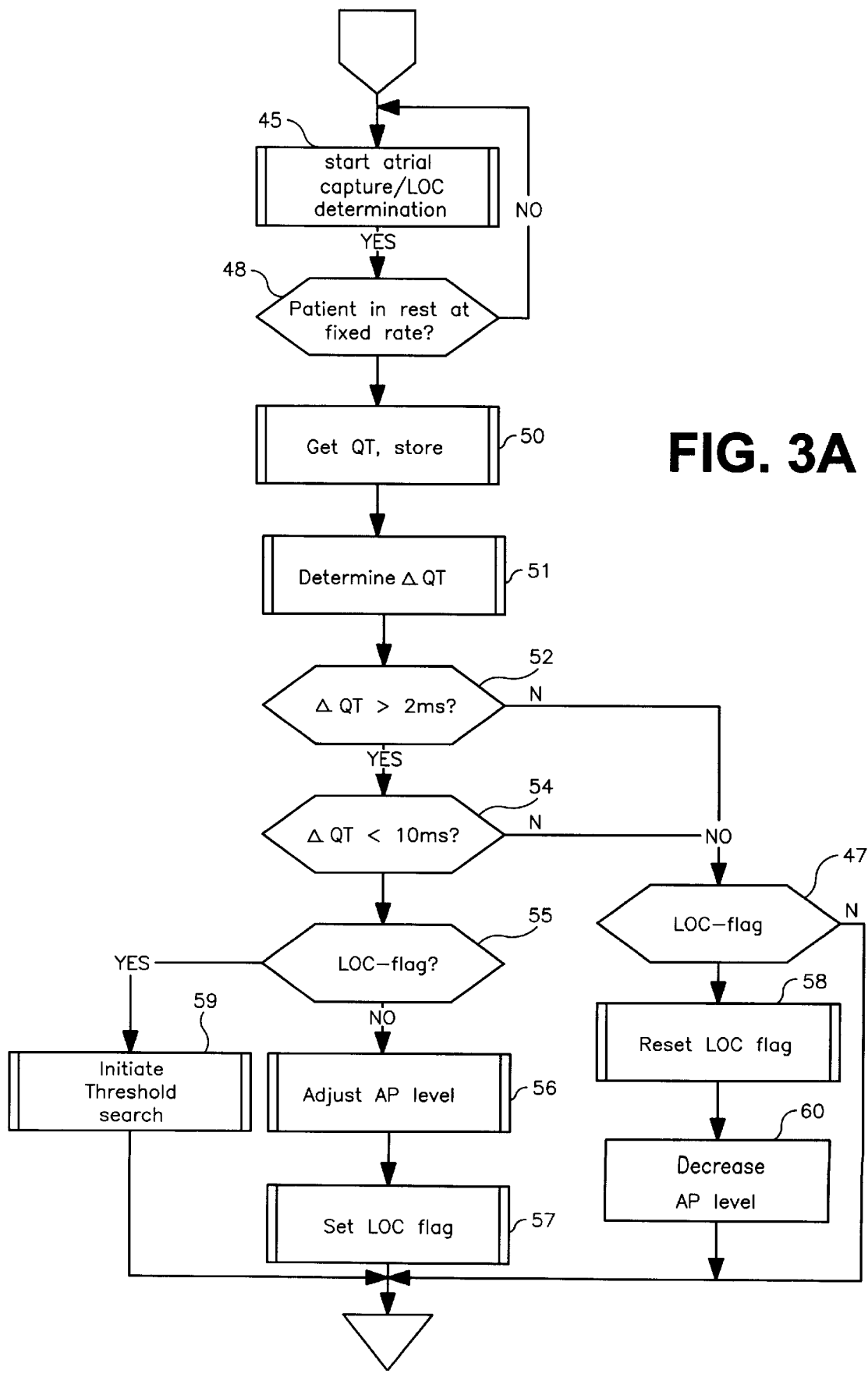
FIG. 3A is a flow diagram showing the primary steps taken cyclically in determining whether a delivered AP results in capture or LOC.

Referring now to FIG. 3A, there is shown a flow diagram indicating the primary logic steps taken in the pacemaker system of this invention. It is to be understood that this flow diagram provides only the primary steps for determining atrial loss of capture, and does not show other known steps which a DDD type pacemaker takes cyclically for pacing and sensing in the atrium and ventricle. The flow diagram of FIG. 3 is entered after delivery of a VP. At 45, the pacemaker starts the atrial capture/LOC determination. At 48, it is determined whether the patient is at rest. This is a necessary condition, because otherwise variations in QT can be introduced by response to the patient's physiological demands. Thus, the determination can only be made as long as the patient is being paced at a fixed rate. At 50, the pacemaker gets and stores the QT interval. At 51, the difference between the presently obtained value and the last value of QT is obtained, providing ()QT. Next, at 52, )QT is compared with a predetermined lower limit, e.g., 2 ms. If it is less than 2 ms, this indicates capture, and the routine exits to block 47. If )QT is greater than 2 ms, then the routine goes to block 54, and determines if it is less than an upper limit, e.g. 10 ms. If no, this suggests spontaneous beats and no failure of atrial capture, so the routine goes to block 47. But if yes at 54, this confirms that )QT is within the predetermined range, and at 55 it is determined if the LOC flag is set. If yes, which means that there has been failure to capture during the previous cycle as well, the routine goes to block 59 and initiates a threshold search. If the LOC flag is not set, then at 56 the pacemaker adjusts the AP level, e.g., increases it by a predetermined increment. Then at 57, the LOC flag is set, indicating that LOC was determined at the last cycle.

Returning to block 47, the routine comes to this point if )QT does not indicate LOC. If the LOC flag is already set, this means that there was an atrial LOC at the last previous )QT determination, and that the AP level had been incremented. Accordingly, the routine resets the LOC flag at 58, and decreases the AP level at 60. If the LOC flag is not set at 47, the routine exits.

Figure 3B:
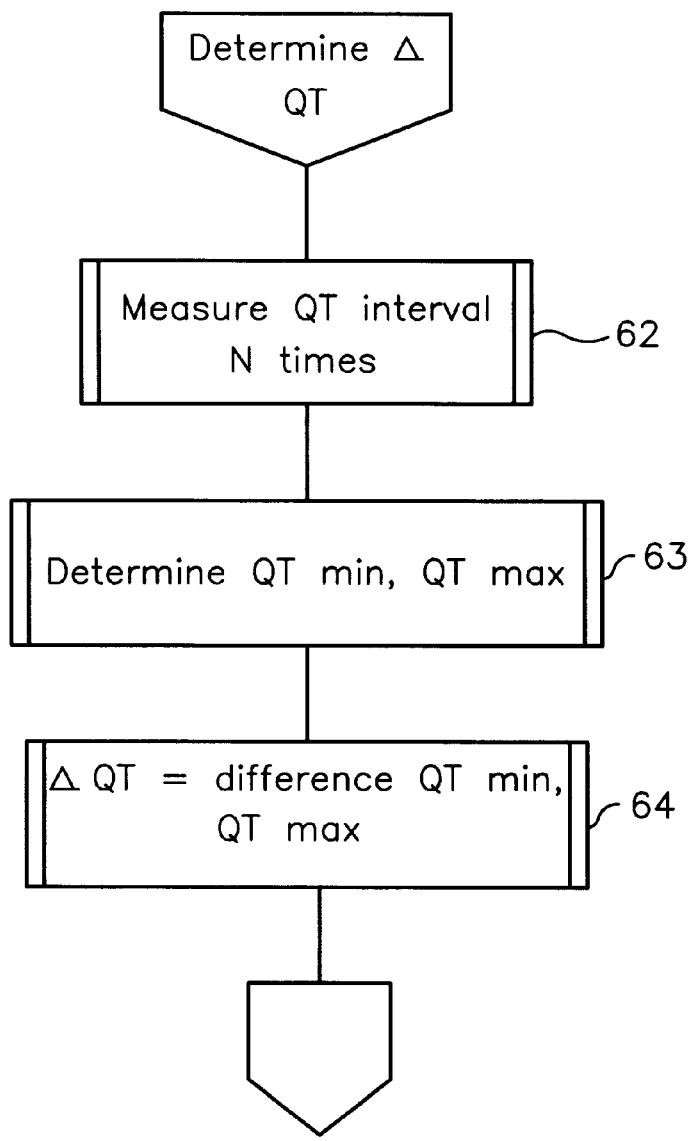
FIG. 3B is a flow diagram of a specific routine for determining $\Delta QT$.

Referring now to FIG. 3B, there is shown a flow diagram of an embodiment of the steps taken in obtaining a measure of )QT. It is to be noted that from beat to beat there may be QT variations which constitute noise, and do not accurately reflect whether or not there has been atrial capture. Accordingly, in this embodiment the QT interval is measured N times over successive cycles, as indicated at 62, where N is a programmable variable. At 63, the pacemaker determines the minimum and maximum values of QT, and at 64 )QT is determined as QTmax-QTmin. This difference value is taken as the measure of )QT, and used in the remainder of the routine shown in FIG. 3A. It is to be noted that other variations of determining )QT may also be used, i.e., )QT can be calculated each beat as a running average of the beat-to-beat change in QTint over N beats.

It is to be understood that other arrangements for responding to atrial LOC can be utilized within the scope of the invention. Further, the determination of atrial LOC can be made by inspecting other features of the QRS and T waves, such that occurrence of atrial LOC can be determined simply by examining the ventricular signals, and without the need to collect other data. It is seen that the invention provides the advantage of a simple determination of atrial LOC, particularly in a patent with AV block.

What is claimed is:

1. A dual chamber pacemaker system, said system having atrial pace means for delivering atrial pacing pulses to a patient's atrium, ventricular pace means for delivering ventricular pace pulses to the patient's ventricle, and sense means for sensing signals from the patient's ventricle, comprising:

QT means operative over successive pacemaker cycles for determining the QT interval;

difference means for determining change in said QT interval;

range means for determining whether said change is within a predetermined range; and LOC means for determining atrial loss of capture when said QT change is not within said range.

2. The system as described in claim 1, comprising level means for setting the energy level of said atrial pacing pulses, and response means for responding to a determination of atrial loss of capture by controlling said level means to reset the energy level of delivered atrial pacing pulses.

3. The system as described in claim 2, wherein said response means comprises search means for carrying out a threshold search to determine atrial threshold, and means for controlling said level means to set said energy level at a safe level above determined atrial threshold.

4. The system as described in claim 2, wherein said response means comprises increment means for controlling said level means to increment said energy level by a predetermined value.

5. The system as described in claim 1, wherein said range means comprises means for defining said range as about 2 ms to 10 ms.

6. The system as described in claim 1, wherein said range means comprises programmable means for receiving data for programming said range.

7. The system as described in claim 1, wherein said range means comprises means for defining said range as being greater than about 2 ms.

8. The system as described in claim 1, wherein said difference means comprises means for obtaining a measure of change in QT interval over N successive beats.

9. In a DDD-type pacing system, a method of determining when a delivered atrial pace pulse does not capture the patient's atrium, comprising:

successively delivering atrial pace pulses at a controllable energy level and with a substantially fixed rate, and delivering a ventricular pace pulse at a predetermined AV interval following each atrial pace pulse to produce ventricular beats;

determining the QT interval associated with each ventricular beat;

determining a measure of the change of QT intervals corresponding to said ventricular beats;

determining when said QT change measure does not meet predetermined criteria; and determining that an atrial pace pulse did not capture the patient's atrium when said QT change measure does not meet said criteria.

10. The method as described in claim 9, comprising determining whether said QT difference is within a predetermined range.

11. The method as described in claim 10, comprising determining whether said QT change measure is within a range of about 2 ms to 10 ms.

* * * * *

UNITED STATES PATENT AND TRADEMARK OFFICE
CERTIFICATE OF CORRECTION

PATENT NO.    : 6,216,037 B1
DATED         : April 10, 2001
INVENTOR(S)   : Van Oort It is certified that error appears in the above-identified patent and that said Letters Patent is hereby corrected as shown below:

Column 1,
Line 8, change "of for" to -- of --.

Signed and Sealed this

Twenty-fifth Day of March, 2003

JAMES E. ROGAN
*Director of the United States Patent and Trademark Office*